United States Patent
Ramesh et al.

(10) Patent No.: US 11,865,597 B2
(45) Date of Patent: Jan. 9, 2024

(54) METHOD FOR BIOREMEDIATION OF LEAD

(71) Applicants: Sunil Kumar Channarayapatna Ramesh, Channarayapatna (IN); Emmanuel Stephen Victor, Boston, MA (US); Kishore Babu Naripogu, Okayama (JP); Geetha Nagaraja, Mysuru (IN)

(72) Inventors: Sunil Kumar Channarayapatna Ramesh, Channarayapatna (IN); Emmanuel Stephen Victor, Boston, MA (US); Kishore Babu Naripogu, Okayama (JP); Geetha Nagaraja, Mysuru (IN)

(73) Assignee: Seed Health Inc., Venice, CA (US)

( * ) Notice: Subject to any disclaimer, the term of this patent is extended or adjusted under 35 U.S.C. 154(b) by 311 days.

(21) Appl. No.: 17/000,663

(22) Filed: Aug. 24, 2020

(65) Prior Publication Data
US 2021/0053096 A1    Feb. 25, 2021

Related U.S. Application Data

(60) Provisional application No. 62/890,827, filed on Aug. 23, 2019.

(51) Int. Cl.
| | |
|---|---|
| *B09C 1/10* | (2006.01) |
| *C02F 3/34* | (2023.01) |
| *C12N 1/20* | (2006.01) |
| *C02F 101/20* | (2006.01) |

(52) U.S. Cl.
CPC ............ *B09C 1/10* (2013.01); *C02F 3/347* (2013.01); *C12N 1/20* (2013.01); *C02F 2101/20* (2013.01); *C02F 2305/06* (2013.01); *C12N 2500/12* (2013.01); *C12N 2500/16* (2013.01); *C12N 2500/32* (2013.01); *C12N 2500/74* (2013.01); *C12N 2501/998* (2013.01)

(58) Field of Classification Search
None
See application file for complete search history.

(56) References Cited

U.S. PATENT DOCUMENTS

| | | |
|---|---|---|
| 5,053,139 A | 10/1991 | Dodwell et al. |
| 5,833,855 A | 11/1998 | Saunders |
| 2004/0222151 A1 | 11/2004 | Lee et al. |
| 2017/0341963 A1 | 11/2017 | Woodward |

FOREIGN PATENT DOCUMENTS

| | | |
|---|---|---|
| CN | 104327859 | 2/2015 |
| WO | WO 2003/011487 | 2/2003 |

OTHER PUBLICATIONS

Gayatri et al., "Biosorption of lead by Bacillus licheniformis isolated from E-waste landfill" International Journal of Bioassays, 6.02 (2017):5240-5244. DOI: dx.doi.org/10.21746/ijbio.2017.02.003.*
Syed, S. & Chinthala, P., "Heavy Metal Detoxification by Different Bacillus Species Isolated from Solar Salterns", Scientifica vol. 2015, Article ID 319760, 8 pages. DOI: dx.doi.org/10.1155/2015/319760.*
Carlos et al. "Irrigation of paddy soil with industrial landfill leachate: impacts in rice productivity, plant nutrition, and chemical characteristics of soil," Paddy and Water Environment, Jan. 2017, vol. 15, pp. 133-144 (Abstract Only).
Mayer et al. "Preparation of media and buffers with soluble lead," Analytical Biochemistry, Mar. 2006, vol. 356, No. 1, pp. 142-144 (Abstract Only).
Mire et al. "Lead precipitation by Vibrio harveyi: evidence for novel quorum-sensing interactions," Applied and Environmental Microbiology, Feb. 2004, vol. 70, No. 2, pp. 855-864.
Sambrook et al. "Molecular Cloning: A Laboratory Manual," 1989 2nd ed. (Abstract Only).
Zhu et al. "*Burkholderia dabaoshanensis* sp. nov., a Heavy-Metal-Tolerant Bacteria Isolated from Dabaoshan Mining Area Soil in China," PLoS ONE, Dec. 2012, vol. 7, No. 12, e50225, 7 pages.

* cited by examiner

*Primary Examiner* — Suzanne M Noakes
(74) *Attorney, Agent, or Firm* — Sheridan Ross P.C.

(57) ABSTRACT

The present disclosure provides methods and compositions of matter directed to removing heavy metals, such as lead, from aqueous solutions by bioremediation. The methods use bacteria, which thrive in the presence of heavy metals to precipitate the heavy metals from the aqueous solution. In some embodiments, the bacteria comprise *Bacillus licheniformis*.

10 Claims, 7 Drawing Sheets

Specification includes a Sequence Listing.

METHOD FOR BIOREMEDIATION OF LEAD

CROSS-REFERENCE TO RELATED APPLICATION

This application claims the benefit of priority under 35 U.S.C. § 119(e) to U.S. Provisional Patent Application 62/890,827, filed 23 Aug. 2019, the entirety of which is incorporated herein by reference.

REFERENCE TO SEQUENCE LISTING

This application contains a sequence listing submitted as an electronic text file named "10122-1_Sequence Listing_ST25.txt," having a file size of 1,574 bytes and created on Aug. 19, 2020. The information contained in this electronic file is hereby incorporated by reference in its entirety pursuant to 37 C.F.R. § 1.77(b)(5)(i)(B).

FIELD

The present disclosure generally relates to methods for bioremediation of heavy metals, such as lead, from contaminated materials, such as an effluent stream.

BACKGROUND

Industrial processes as well as accidental spills can lead to heavy metals and other contaminants in water. In some places, unregulated or lax enforcement has led to contaminated soils and aquifers. Lead is a dangerous contaminant that leads to health problems, especially in the most vulnerable populations: the young, sick, and elderly. Apart from being hazardous to human health, it also has an adverse effect on the fauna and flora.

Known systems for removing lead typically involve ion exchange, typically using a filtration device, precipitation, osmosis, evaporation, etc. However, these are often costly and not environmentally friendly. Bioremediation is defined as a waste management technique that involves the use of micro-organisms, such as bacteria, to remove or neutralize pollutants from a contaminated site. According to the EPA, bioremediation is a "treatment that uses naturally occurring organisms to break down hazardous substances into less toxic or non-toxic substances."

For purposes of further disclosure and to comply with applicable written description and enablement requirements, the following references generally relate to systems and methods for bioremediation and reducing and removing heavy metals from a solution and are hereby incorporated by reference in their entireties: U.S. Pat. Nos. 5,053,139; 5,833,855; U.S. Patent Publication No. 2004/0222151; U.S. Patent Publication No. 2017/0341963; PCT Application No. PCT/US02/24001 (WO2003/011487A1); Chinese Patent No. CN 104327859 A.

In the case of lead removal, bioremediation has proven difficult. Bacterial solutions have been elusive because typically bacteria do not thrive in high-lead environments. However, such methods are preferred because they are not energy intensive, and bioremediation generally does not have hazardous byproducts. Accordingly, there exists a need for methods and systems for bioremediation of heavy metals, such as lead, from contaminated materials.

SUMMARY

In one embodiment, the present invention includes a method for bioremediation of a waste material comprising lead. The method includes inoculating *Bacillus licheniformis* bacteria in an aqueous culture medium comprising casamino acids and lead, growing the bacteria in the aqueous culture medium for a period of time, contacting the medium with the contaminated material and precipitating at least some of the lead present in the contaminated material. The period of time may be at least 24 hours, at least 48 hours, at least 60 hours, or at least 72 hours.

In one embodiment, the present invention includes a method of culturing lead tolerant *Bacillus licheniformis*. This method includes inoculating *Bacillus licheniformis* bacteria into an aqueous culture medium comprising casamino acids and lead and growing the bacteria in the aqueous culture medium for a period of time. The period of time may be at least 24 hours, at least 48 hours, at least 60 hours, or at least 72 hours.

In one embodiment, the present invention includes an aqueous culture medium comprising casamino acids at a concentration of about 2.5 g/L to about 10 g/L, sodium chloride at a concentration of about 3 g/L to about 12 g/L, magnesium sulfate at a concentration of about 3.5 g/L to about 15 g/L, yeast extract at a concentration of about 4 g/L to about 16 g/L, and peptone at a concentration of about 4 g/L to about 18 g/L.

In one embodiment, the present invention includes an aqueous culture medium consisting essentially of, or consisting of, casamino acids at a concentration of about 2.5 g/L to about 10 g/L, sodium chloride at a concentration of about 3 g/L to about 12 g/L, magnesium sulfate at a concentration of about 3.5 g/L to about 15 g/L, yeast extract at a concentration of about 4 g/L to about 16 g/L, and peptone at a concentration of about 4 g/L to about 18 g/L.

This Summary is neither intended nor should it be construed as being representative of the full extent and scope of the present disclosure. The present disclosure is set forth in various levels of detail in the Summary as well as in the attached drawings and the Detailed Description, and no limitation as to the scope of the present disclosure is intended by either the inclusion or non-inclusion of elements, components, etc. in this Summary. Additional aspects of the present disclosure will become clearer from the Detailed Description, when taken together with the drawings.

DETAILED DESCRIPTION

Figure 1:
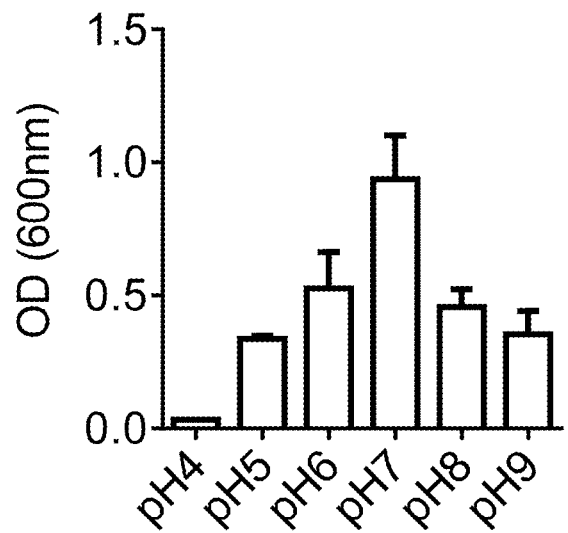
FIG. 1 shows the determination of optimal pH of *Bacillus licheniformis* strain ECOBIO_2.

The present invention is directed at methods and compositions useful for bioremediation of lead using the bacteria *Bacillus licheniformis*. for precipitating heavy metal from a solution. Lead rich solutions have been a particularly difficult solution for bacteria to thrive in, making lead bioremediation difficult. As described herein, the bacteria grown according to this invention exhibit a surprising ability to thrive in rich environments that are rich in lead, and precipitate lead from contaminated aqueous solutions. Thus, the present invention provides low-cost and easy-to-performs methods which lead to robust and reproducible lead precipitation from a solution.

For purposes of further disclosure and to comply with applicable written description and enablement requirements, the following references generally relate to systems and methods for bioremediation and reducing and removing heavy metals from a solution and are hereby incorporated by reference in their entireties:

J. Sambrook et al., *Molecular Cloning: A Laboratory Manual* (2d ed. 1989).

Chad E. Mire et al., "Lead precipitation by *Vibrio harveyi*: evidence for novel quorum-sensing interactions," 70(2) *Applied and Environmental Microbiology* 855 (February 2004).

R. A. Mayer and H. A. Godwin, "Preparation of media and buffers with soluble lead," 356(1) *Analytical Biochemistry* 142 (March 2006).

Honghui Zhu et al., "*Burkholderia dabaoshanensis* sp. nov., a heavy-metal-tolerant bacteria isolated from Dabaoshan mining area soil in China," 7(12) *PLoS ONE* e50225 (December 2012).

Filipe Selau Carlos et al., "Irrigation of paddy soil with industrial landfill leachate: impacts in rice productivity, plant nutrition, and chemical characteristics of soil," 15 *Paddy and Water Environment* 133 (June 2016).

In one aspect, the present invention provides a method for bioremediation of a contaminated material or waste material comprising lead. The method involves the use of *Bacillus licheniformis* bacteria that when grown under conditions described herein can precipitate lead from contaminated aqueous solutions. The method comprises inoculating *Bacillus licheniformis* bacteria in an aqueous culture medium comprising casamino acids and lead; growing the bacteria in the aqueous culture medium for a period of time; contacting the aqueous culture medium with the contaminated or waste material comprising lead; and precipitating at least some of the lead present in contaminated or waste material.

In some embodiments, the *Bacillus licheniformis* comprises the strain ECOBIO_2, which comprises a 16S rRNA gene comprising SEQ ID NO:1 (also deposited as GenBank Accession KP877534.1).

In some embodiments, the medium comprises live *Bacillus licheniformis* bacteria. In some embodiments, prior to contacting, the aqueous culture medium is centrifuged to obtain a supernatant fraction and a fraction enriched in the *Bacillus licheniformis* bacteria. In some embodiments, the supernatant fraction of the medium is added to or contacted with the contaminated or waste material and is sufficient to precipitate lead. Without wishing to be bound by theory, it is believed that the bacteria may secrete certain active factors, such as enzymes, that pass into the supernatant and are able to precipitate lead. In some embodiments, the fraction enriched in the *Bacillus licheniformis* bacteria is added to or contacted with the contaminated or waste material to precipitate lead.

For contacting with the contaminated material, the aqueous culture medium (comprising live bacteria, or comprising only the supernatant) may be provided in any suitable physical form, such as a liquid suspension in the culture medium or any other suitable suspension medium, or a dry or substantially dry form, such as a patty or cake, or a lyophilized powder. In some embodiments, it may be provided in a container that has semipermeable or permeable walls, so that the bacteria present in the medium or the active factor in the supernatant is able pass into the contaminated material.

The aqueous culture medium of the present invention comprises casamino acids. Casamino acids is a mixture of amino acids and some very small peptides obtained from acid hydrolysis of casein. It is typically used in microbial growth media. It has all the essential amino acids except tryptophan. It was surprisingly found that *Bacillus licheniformis* grown in a medium containing casamino acids had the ability for lead bioremediation.

The culture medium further comprises a metal salt, yeast extract and peptone. The metal salt may be one or more of sodium chloride, potassium chloride, magnesium sulfate, ammonium sulfate, and Di-potassium hydrogen ortho-phosphate.

In some embodiments, the aqueous culture medium comprises casamino acids, sodium chloride, magnesium sulfate, yeast extract and peptone.

In some embodiments, the casamino acids is present at a concentration of about 1.0 g/L to about 12.0 g/L. For example, in various embodiments the casamino acids may be present at a concentration of about 1.0 g/L, 1.5 g/L, 2.0 g/L, about 2.5 g/L, about 3.0 g/L, about 3.5 g/L, about 4.0 g/L, about 4.5 g/L, about 4.6 g/L, about 4.7 g/L, about 4.8 g/L, about 4.9 g/L, about 5.0 g/L, about 5.1 g/L, about 5.2 g/L, about 5.3 g/L, about 5.4 g/L, about 5.5 g/L, about 6.0 g/L, about 6.5 g/L, about 7.0 g/L, about 7.5 g/L, about 8.0 g/L, about 8.5 g/L, about 9.0 g/L, about 9.5 g/L, about 10.0 g/L, about 10.5 g/L, about 11.0 g/L, about 11.5 g/L, about 12.0 g/L, or any range between any two of the aforementioned numbers such as, 2-12 g/L, 2.5-10 g/L, 3-8 g/L, etc. In some embodiments, the casamino is about 5 g/L.

In some embodiments, the sodium chloride is present at a concentration of about 2.0 g/L to about 15.0 g/L. For example, in various embodiments it may be present at a concentration of about 2.0 g/L, about 2.5 g/L, about 3.0 g/L, about 3.5 g/L, about 4.0 g/L, about 4.5 g/L, about 5.0 g/L, about 5.5 g/L, about 6.0 g/L, about 6.1 g/L, about 6.2 g/L, about 6.3 g/L, about 6.4 g/L, about 6.5 g/L, about 6.6 g/L, about 6.7 g/L, about 6.8 g/L, about 6.9 g/L, about 7.0 g/L, about 7.5 g/L, about 8.0 g/L, about 8.5 g/L, about 9.0 g/L, about 9.5 g/L, about 10.0 g/L, about 10.5 g/L, about 11.0 g/L, about 11.5 g/L, about 12.0 g/L, about 12.5 g/L, about 13.0 g/L, about 13.5 g/L, about 14.0 g/L, about 14.5 g/L, about 15.0 g/L, or a range between any two of the aforementioned numbers such as about 3-12 g/L, 5-7 g/L, etc. In some embodiments, the sodium chloride is about 6.25 g/L.

In embodiments, the magnesium sulfate is present at a concentration of about 2.0 g/L to about 20.0 g/L. For example, in various embodiments it may be present at a concentration of about 2.0 g/L, about 2.5 g/L, about 3.0 g/L, about 3.5 g/L, about 4.0 g/L, about 4.5 g/L, about 5.0 g/L, about 5.5 g/L, about 6.0 g/L, about 6.5 g/L, about 7.0 g/L, about 7.1 g/L, about 7.2 g/L, about 7.3 g/L, about 7.4 g/L, about 7.5 g/L, about 7.6 g/L, about 7.7 g/L, about 7.8 g/L, about 7.9 g/L, about 8.0 g/L, about 8.5 g/L, about 9.0 g/L, about 9.5 g/L, about 10.0 g/L, about 10.5 g/L, about 11.0 g/L, about 11.5 g/L, about 12.0 g/L, about 12.5 g/L, about 13.0 g/L, about 13.5 g/L, about 14.0 g/L, about 14.5 g/L, about 15.0 g/L, about 15.5 g/L, about 16.0 g/L, about 16.5 g/L, about 17.0 g/L, about 17.5 g/L, about 18.0 g/L, about 18.5 g/L, about 19.0 g/L, about 19.5 g/L, about 20.0 g/L, or a range between any two of the aforementioned numbers such as, about 3.5-15 g/L, 7-8 g/L. In some embodiments, the magnesium sulfate is about 7.5 g/L.

In some embodiments, the yeast extract is present at a concentration of about 3 g/L to about 20 g/L. For example, in various embodiments it may be present at a concentration of about 3.0 g/L, about 3.5 g/L, about 4.0 g/L, about 4.5 g/L, about 5.0 g/L, about 5.5 g/L, about 6.0 g/L, about 6.5 g/L, about 7.0 g/L, about 7.5 g/L, about 7.6 g/L, about 7.7 g/L, about 7.8 g/L, about 7.9 g/L, about 8.0 g/L, about 8.1 g/L, about 8.2 g/L, about 8.3 g/L, about 8.4 g/L, about 8.5 g/L, about 9.0 g/L, about 9.5 g/L, about 10.0 g/L, about 10.5 g/L, about 11.0 g/L, about 11.5 g/L, about 12.0 g/L, about 12.5 g/L, about 13.0 g/L, about 13.5 g/L, about 14.0 g/L, about 14.5 g/L, about 15.0 g/L, about 15.5 g/L, about 16.0 g/L, about 16.5 g/L, about 17.0 g/L, about 17.5 g/L, about 18.0 g/L, about 18.5 g/L, about 19.0 g/L, about 19.5 g/L, about 20.0 g/L, or a range between any two of the aforementioned numbers such as, about 4-16 g/L, 7-9 g/L, etc. In some embodiments, the magnesium sulfate is about 8 g/L.

In some embodiments, the peptone is present at a concentration of about 3 g/L to about 20 g/L. For example, in various embodiments it may be present at a concentration of about 3.0 g/L, about 3.5 g/L, about 4.0 g/L, about 4.5 g/L, about 5.0 g/L, about 5.5 g/L, about 6.0 g/L, about 6.5 g/L, about 7.0 g/L, about 7.5 g/L, about 8.0 g/L, about 8.1 g/L, about 8.2 g/L, about 8.3 g/L, about 8.4 g/L, about 8.5 g/L, about 8.6 g/L, about 8.7 g/L, about 8.8 g/L, about 8.9 g/L, about 9.0 g/L, about 9.1 g/L, about 9.2 g/L, about 9.3 g/L, about 9.4 g/L, about 9.5 g/L, about 10.0 g/L, about 10.5 g/L, about 11.0 g/L, about 11.5 g/L, about 12.0 g/L, about 12.5 g/L, about 13.0 g/L, about 13.5 g/L, about 14.0 g/L, about 14.5 g/L, about 15.0 g/L, about 15.5 g/L, about 16.0 g/L, about 16.5 g/L, about 17.0 g/L, about 17.5 g/L, about 18.0 g/L, about 18.5 g/L, about 19.0 g/L, about 19.5 g/L, about 20.0 g/L, or a range between any two of the aforementioned numbers such as, about 4-18 g/L, 6-12 g/L, 8-10 g/L, etc. In some embodiments, the peptone is about 9 g/L.

In some embodiments, the aqueous culture medium comprises casamino acids at a concentration of about 2.5 g/L to about 10 g/L, sodium chloride at a concentration of about 3 g/L to about 12 g/L, magnesium sulfate at a concentration of about 3.5 g/L to about 15 g/L, yeast extract at a concentration of about 4 g/L to about 16 g/L, and peptone at a concentration of about 4 g/L to about 18 g/L.

In some embodiments, the aqueous culture medium comprises casamino acids at a concentration of about 5 g/L, sodium chloride at a concentration of about 6.25 g/L, magnesium sulfate at a concentration of about 7.5 g/L, yeast extract at a concentration of about 8 g/L, and peptone at a concentration of about 9 g/L.

For the bacteria to develop the ability to grow in a lead containing environment, the aqueous culture medium described herein comprises lead. In embodiments, the concentration of lead in the aqueous culture medium is about 0.01 mM to about 10 mM. In some embodiments, the concentration of lead in the aqueous culture medium is in the range of about 0.1 mM to about 6.0 mM. In some embodiments, the concentration of lead in the aqueous culture medium is in the range of about 0.1 mM to about 4.0 mM. In some embodiments, the concentration of lead in the aqueous culture medium is in the range of about 0.2 mM to about 2.5 mM.

For example, in various embodiments the concentration of lead in the aqueous culture medium may be about 0.01 mM, 0.05 mM, 0.1 mM, 0.15 mM, 0.20 mM, 0.25 mM, 0.25 mM, 0.30 mM, 0.35 mM, 0.40 mM, 0.45 mM, 0.50 mM, 0.55 mM, 0.60 mM, 0.65 mM, 0.70 mM, 0.75 mM, 0.80 mM, 0.85 mM, 0.90 mM, 0.95 mM, 1.0 mM, 1.50 mM, 1.6 mM, 1.7 mM, 1.8 mM, 1.9 mM, 2.0 mM, 2.1 mM, 2.2 mM, 2.3 mM, 2.4 mM, 2.50 mM, 3.0 mM, 3.50 mM, 4.0 mM, 4.5 mM, 5.0 mM, 5.5 mM, 6.0 mM, 6.5 mM, 7.0 mM, 7.5 mM, 8.0 mM, 8.5 mM, 9.0 mM, 9.5 mM, 10.0 mM, or a range between any two of the aforementioned numbers such as, about 0.05 mM-6.0 mM or 0.1-4.0 mM. In some embodiments, the concentration of lead in the aqueous culture medium is about 0.50 mM. In some embodiments, the concentration of lead in the aqueous culture medium it is about 2 mM.

In some embodiments, the bacteria are grown in the aqueous culture medium comprising lead for at least about 12 hours, at least about 24 hours, at least about 36 hours, at least about 48 hours, at least about 60 hours, at least about 72 hours, at least about 84 hours, at least about 96 hours, at least about 108 hours, at least about 120 hours, at least about 132 hours, at least about 144 hours, at least about 156 hours, or at least about 168 hours. In some embodiments, the bacteria are grown for at least about 1 day, at least about 2 days, at least about 3 days, at least about 4 days, at least about 5 days, at least about 6 days, or at least about 7 days. In some embodiments, the bacteria are grown for at least about 48 hours, at least 60 hours, or at least 72 hours. In some embodiments, they are grown for at least about 72 hours. After the bacteria are grown in the medium for enough time, they become lead tolerant (or lead resistant) and acquire the surprising ability of to precipitate lead (lead bioremediation).

In some embodiments, the bacteria are grown at a temperature of about 20° C. to about 50° C., about 25° C. to about 40° C. In some embodiments, the bacteria are incubated at a temperature of about 37° C. In Some embodiments, the pH of the aqueous culture medium is about 4 to about 10, or about 5 to about 9. In some embodiments, the pH of the aqueous culture medium is about 7.

The contaminated material may be any aqueous solution that is contaminated with lead. The material may be taken from any aqueous stream, such as a river, lake, lagoon, or any other water body that is contaminated with water. It may also be an effluent stream from a factory. The concentration of lead in the contaminated material may range from about 0.01 mM to about 100.0 mM. The bacteria grown according to the present invention may be added directly to a contaminated or waste stream to effect lead bioremediation. In some embodiments, at least about 25%, 30%, 35%, 40%, 45%, 50%, 55%, 60%, 65%, 70%, 75%, 80%, 85%, 90%, 95% lead present in the contaminated or waste material may be precipitated. In some embodiments, at least about 25% lead present in the contaminated or waste material may be precipitated. In some embodiments, at least about 50% lead present in the contaminated or waste material may be precipitated. In some embodiments, at least about 60% lead present in the contaminated or waste material may be precipitated. In some embodiments, at least about 70% lead present in the contaminated or waste material may be precipitated. In some embodiments, at least about 80% lead present in the contaminated or waste material may be precipitated. In some embodiments, at least about 90% lead present in the contaminated or waste material may be precipitated. In some embodiments, substantially all of the lead present in the contaminated or waste material may be precipitated.

In some embodiments, the method further comprises the step of recovering the lead resistant bacteria. Such bacteria may be stored as a frozen stock and may be thawed and revived and used directly for lead remediation. In some cases, the stored bacteria may need to be first grown in aqueous culture media described herein comprising lead and re-acclimatized before using in lead remediation.

In some embodiments, the method comprises the step of recovering the precipitated lead from the contaminated or waste material. The recovery may be done using any known methods in the art, such as filtration. In some embodiments, at least about 25%, 30%, 35%, 40%, 45%, 50%, 55%, 60%, 65%, 70%, 75%, 80%, 85%, 90%, 95%, 96%, 97%, 98%, or 99% precipitated lead may be recovered. In some embodiments, at least about 25% precipitated lead may be recovered. In some embodiments, at least about 50% precipitated lead may be recovered. In some embodiments, at least about 60% precipitated lead may be recovered. In some embodiments, at least about 70% precipitated lead may be recovered. In some embodiments, at least about 80% precipitated lead may be recovered. In some embodiments, at least about 90% precipitated lead may be recovered. In some embodiments, at least about 95% precipitated lead may be recovered. In some embodiments, substantially all of the precipitated lead may be recovered.

In another aspect, the present invention includes a method of culturing lead tolerant *Bacillus licheniformis* bacteria. The method comprises inoculating *Bacillus licheniformis* bacteria into an aqueous culture medium comprising casamino acids and lead; and growing the bacteria in the aqueous culture medium for a period of time. The period of time may be at least 24 hours, at least 36 hours, at least 48 hours, at least 60 hours, or at least 72 hours. Such bacteria develop the ability of lead remediation. In some embodiments, the method further comprises the step of recovering the lead tolerant (or lead resistant) bacteria. Such bacteria may be stored, for example as a frozen stock, and may be thawed and revived and used directly for lead remediation. In some cases, the stored bacteria may need to be first grown in an aqueous culture medium comprising casamino acids and lead and re-acclimatized before using in lead remediation.

In another aspect, the present invention includes an aqueous culture medium comprising casamino acids at a concentration of about 2.5 g/L to about 10 g/L, sodium chloride at a concentration of about 3 g/L to about 12 g/L, magnesium sulfate at a concentration of about 3.5 g/L to about 15 g/L, yeast extract at a concentration of about 4 g/L to about 16 g/L, and peptone at a concentration of about 4 g/L to about 18 g/L. In some embodiments, the aqueous culture medium comprises casamino acids at a concentration of about 5 g/L, sodium chloride at a concentration of about 6.25 g/L, magnesium sulfate at a concentration of about 7.5 g/L, yeast extract at a concentration of about 8 g/L, and peptone at a concentration of about 9 g/L.

In another aspect, the present invention includes an aqueous culture medium consisting essentially of, or consisting of, casamino acids at a concentration of about 2.5 g/L to about 10 g/L, sodium chloride at a concentration of about 3 g/L to about 12 g/L, magnesium sulfate at a concentration of about 3.5 g/L to about 15 g/L, yeast extract at a concentration of about 4 g/L to about 16 g/L, and peptone at a concentration of about 4 g/L to about 18 g/L. In some embodiments, the aqueous culture medium consists essentially of, or consists of, casamino acids at a concentration of about 5 g/L, sodium chloride at a concentration of about 6.25 g/L, magnesium sulfate at a concentration of about 7.5 g/L, yeast extract at a concentration of about 8 g/L, and peptone at a concentration of about 9 g/L.

The phrases "at least one," "one or more," and "and/or," as used herein, are open-ended expressions that are both conjunctive and disjunctive in operation. For example, each of the expressions "at least one of A, B and C," "at least one of A, B, or C," "one or more of A, B, and C," "one or more of A, B, or C," and "A, B, and/or C" means A alone, B alone, C alone, A and B together, A and C together, B and C together, or A, B and C together.

The term "a" or "an" entity, as used herein, refers to one or more of that entity. As such, the terms "a" (or "an"), "one or more" and "at least one" can be used interchangeably herein.

The use of "including," "comprising," or "having" and variations thereof herein is meant to encompass the items listed thereafter and equivalents thereof as well as additional items. Accordingly, the terms "including," "comprising," or "having" and variations thereof can be used interchangeably herein.

Unless otherwise indicated, all numbers expressing quantities, dimensions, conditions, ratios, ranges, and so forth used in the specification and claims are to be understood as being modified in all instances by the term "about" or "approximately." Accordingly, unless otherwise indicated, all numbers expressing quantities, dimensions, conditions, ratios, ranges, and so forth used in the specification and claims may be increased or decreased by approximately 5% to achieve satisfactory results. In addition, all ranges described herein may be reduced to any sub-range or portion of the range.

The following examples are provided for the purpose of illustration and are not intended to limit the scope of the present invention. It should be understood that the disclosure is not necessarily limited to the embodiments illustrated herein. As will be appreciated, other embodiments are possible using, alone or in combination, one or more of the features set forth herein. For example, it is contemplated that various features and devices shown and/or described with respect to one embodiment may be combined with or substituted for features or devices of other embodiments regardless of whether or not such a combination or substitution is specifically shown or described herein. Each publication, sequence or other reference disclosed below and elsewhere herein is incorporated herein by reference in its entirety, to the extent that there is no inconsistency with the present disclosure.

Example 1

This Example illustrates the optimal physiological conditions of bioremediation potential *Bacillus licheniformis*.

A lead bio-precipitation (LBP) medium, a Luria Bertain agar (LB) medium, a minimal glucose yeast extract (MGY) medium, and an MGY medium supplemented with casamino acids were obtained or prepared according to the compositions given in Tables 1 through 4.

TABLE 1

Composition of lead bio-precipitation (LBP) medium

| Ingredient | Amount in g/L |
|---|---|
| Sodium chloride (NaCl) | 6.25 |
| Yeast extract | 8 |
| Casamino acids | 5 |
| Peptone | 9 |
| Magnesium sulfate (MgSO$_4$) | 7.5 |
| Distilled water | 1000 mL |

TABLE 2

Composition of Luria Bertain agar (LB) medium

| Ingredient | Amount in g/L |
|---|---|
| Bacto-tryptone | 10 |
| Yeast extract | 5 |
| Sodium chloride (NaCl) | 10 |
| Agar | 10 |
| Distilled water | 1000 |

TABLE 3

Composition of minimum glucose yeast extract (MGY) medium

| Ingredients | Amount in g/L |
|---|---|
| Potassium chloride (KCl) | 0.1 |
| Magnesium sulfate (MgSO$_4$•7H$_2$O) | 0.25 |
| Ammonium sulfate ((NH$_4$)$_2$SO$_4$) | 2 |
| Di-potassium hydrogen ortho-phosphate (K$_2$HPO$_4$) | 0.25 |
| Glucose | 1 |
| Yeast extract | 0.1 |
| Agar | 10 |
| Distilled water | 1000 |

TABLE 4

Composition of MGY with casamino acids

| Ingredients | Amount in g/l |
|---|---|
| Casamino acids | 0.5 |
| Potassium chloride (KCl) | 0.1 |
| Magnesium sulfate (MgSO$_4$•7H$_2$O) | 0.25 |
| Ammonium sulfate ((NH$_4$)$_2$SO$_4$) | 2 |
| Di-potassium hydrogen ortho-phosphate (K$_2$HPO$_4$) | 0.25 |
| Glucose | 1 |
| Yeast extract | 0.1 |
| Agar | 10 |
| Distilled water | 1000 |

Late lag phase cells of *B. licheniformis* were harvested after 24 hours of incubation from a pre-cultured flask. The concentration of bacterial cells was spectrophotometrically adjusted to have an OD of 1.0 at A600 nm. 1 ml of the inoculum was inoculated to 100 ml of sterile LB broth (see Table 2) with a varied pH range of 4, 5, 6, 7, 8, and 9 adjusted using 1N NaOH and 1N HCl. The flasks were incubated at 37° C.

Similarly, to determine the optimal temperature of strain ECOBIO_2, sterilized 100 ml of LB broth was inoculated with 1.0 ml of pre-determined bacterial cells adjusted spectrophotometrically to OD 1.0 at A600 nm. Flasks were then incubated at different temperatures, i.e. 4° C., 25° C., 35° C., 37° C., and 40° C. Each experiment was performed in duplicates. The turbidity of the medium was measured every 24 hours for three days at A600 using spectrophotometer to determine the optimal physiological conditions. The turbidity of the medium was measured in terms of OD. Results are shown in FIG. 1. Significant variation was noticed with respect to varied pH conditions the optimum pH for the growth of strain ECOBIO_2, was 7. However, the bacteria thrived well under both acidic and alkaline conditions. Thus, *B. licheniformis* is well suited to withstand the opposable pH extremities under ex situ and in situ set-ups.

Figure 2:
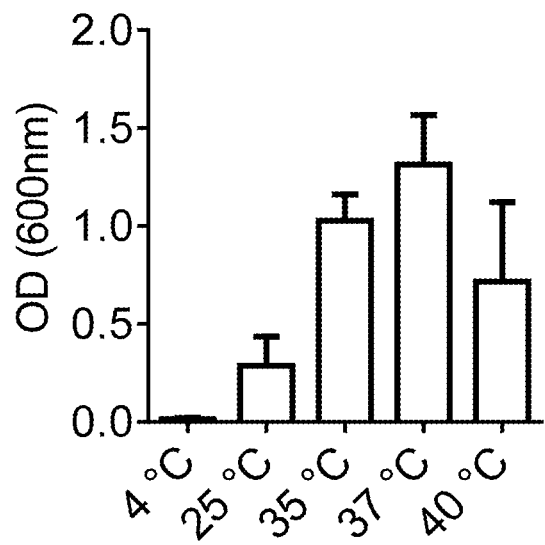
FIG. 2 shows the determination of optimal temperature of *Bacillus licheniformis* strain ECOBIO_2.

Three independent experiments were performed to determine the optimal temperature tolerance of strain ECOBIO_2. Five sets of culture media were prepared and incubated at temperatures of 4° C., 25° C., 35° C., 37° C., and 40° C., respectively. Growth was recorded in terms of OD spectrophotometrically. Results are shown in FIG. 2, which indicate that 37° C. is an optimal temperature for *B. licheniformis* strain ECOBIO_2.

Example 2

This example illustrates the heavy metal acceptability of *B. licheniformis* strain ECOBIO_2.

The pure cultures of each isolates were grown in LB broth and the bacterial cell concentration was spectrophotometrically adjusted to have an OD of 1.0 at A600 nm. 1 ml of cells were inoculated to 100 ml of sterilize LB medium amended with either 1 mM Pb(C$_2$H$_3$O$_2$)$_2$, CdCl$_2$, K$_2$Cr$_2$O$_7$ or with 0.3 mM HgCl$_2$ in individual culture flasks. Flasks were incubated at 37° C. and 150 rpm. The growth rate was measured by assessing the turbidity of the medium every 24 hours after initial incubation for 3 days.

Figure 3:
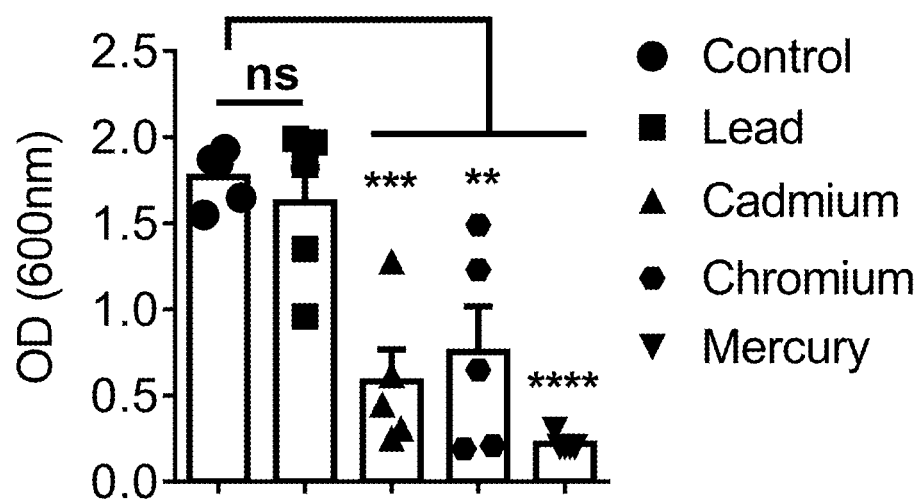
FIG. 3 shows the growth of *Bacillus licheniformis* strain ECOBIO_2 in the presence of different heavy metal salts.

Data obtained from three independent experiments performed to determine the heavy metal acceptability of strain ECOBIO_2. Results (shown in FIG. 3) demonstrated that *B. licheniformis* strain ECOBIO_2 could grow in the presence of lead similar to controls (LB alone). This signifies the noteworthy characteristics of bacteria towards tolerating Pb$^{2+}$ toxicity. However, the growth of *B. licheniformis* strain ECOBIO_2 was significantly reduced in the presence of cadmium, chromium, and mercury with mercury being the most toxic metal among the tested heavy metals.

Example 3

This example illustrates the ability of *B. licheniformis* strain ECOBIO_2 to precipitate lead from lead-containing media.

*B. licheniformis* strain ECOBIO_2 was first grown in the LBP medium amended with lead for 72-96 hours for acclimatization of the bacteria. Interestingly, although the bacteria could grow in the presence of lead, they did not begin to mediate precipitation of lead until about 72 hours and minimum precipitation at 96 hours. Clear lead precipitation occurred after day 5. Hence to circumvent this the long delay in lead precipitation, acclimatized bacteria (bacteria previously grown in LBP media amended with lead) was used. 1 ml of lead-acclimatized *B. licheniformis* strain ECOBIO_2 spectrophotometrically adjusted to have an OD of 1 at A600 nm was transferred to fresh LBP broth amended with 3.5 mM concentration Pb(C$_2$H$_3$O$_2$)2 in 100 ml of LBP broth.

Figure 4A:
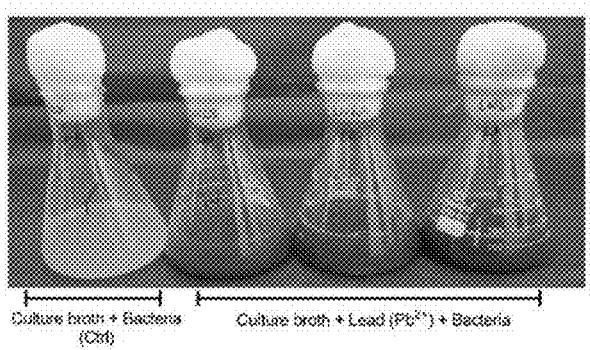
FIGS. 4A through 4D show the ability of *Bacillus licheniformis* strain ECOBIO_2 bacteria to grow in the presence of lead and precipitate the lead present in the culture broth and agar medium.
Figure 4B:
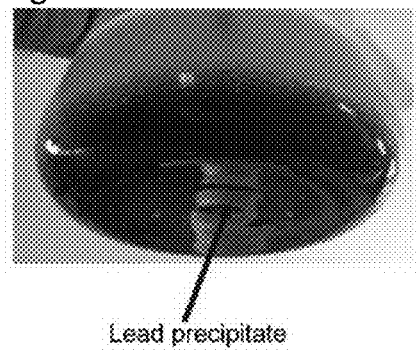
Figure 4C:
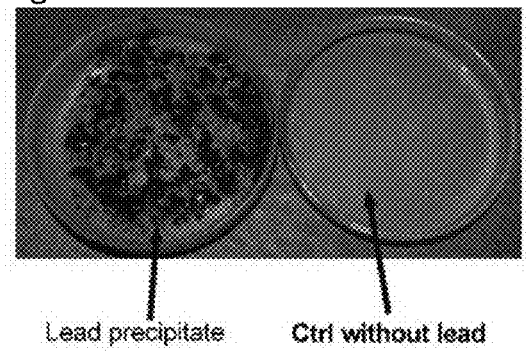
Figure 4D:
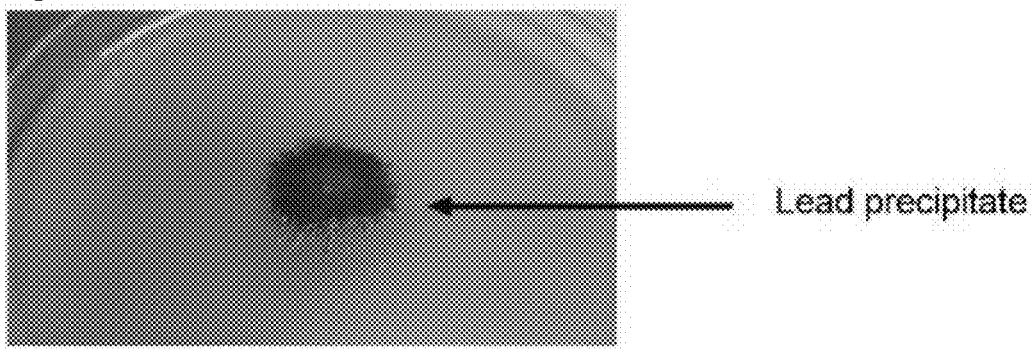

The culture flasks were incubated at 37° C. for 24-48 hours. Culture flasks were kept under continuous observation for the formation of black precipitation. Results are shown in FIGS. 4A through 4D. Upon addition of lead-acclimatized bacteria lead, precipitation was observed in both LBP broth (FIGS. 4A and 4B) and on agar plates (FIGS. 4C and 4D). Precipitation of lead was observed as black precipitate at the bottom of the flask (FIG. 4B).

Example 4

This example illustrates that heat-killed inoculum of Bacillus licheniformis strain ECOBIO_2 does not effectuate lead remediation.

To evaluate the involvement of metabolic process in the bio-precipitation of lead ($Pb^{2+}$), 25 ml of LBP broth with bacterial cells of early lag phase was autoclaved at 121° C. pressure at 20 minutes to kill the cells. Thereafter, the dead cells were harvested by centrifugation at 10,000 rpm for 10 minutes. Harvested cells were inoculated on pre-sterilized LB agar plates to ensure the cellular viability. After 24 hours of incubation by ensuring no growth on LB plates harvested dead cells were used as inoculum. Results shown in FIG. 5F indicated that heat killed bacteria are not able to mediate lead precipitation.

Example 5

This example illustrates the bioavailability to B. licheniformis strain ECOBIO_2 of lead in both chelated and non-chelated forms.

In order to evaluate the bioavailability of $Pb(C_2H_3O_2)_2$ and $Pb(NO_3)_2$ in chelated forms with di-sodium EDTA ($C_{10}H_{14}N_2Na_2O_8$) in 1:2 millimolar ratio ($Pb^{2+}$:EDTA), stock solution of both the Pb' salts 20 mM in 100 ml (650.58 mg/100 ml and 662.4 mg/100 ml for lead acetate and lead nitrate respectively) and EDTA 40 mM/100 ml (1.169 g/100 ml) were prepared in pre-acid washed, clean and dried reagent bottles with distilled water and sterilized. Experiments were performed in duplicates. 250 ml of sterilized LBP broth was used as a microbial growth medium, to which 1:2 mM of [$Pb(C_2H_3O_2)_2$:EDTA], 1 mM of $Pb(C_2H_3O_2)_2$, 1:2 mM of [$Pb(NO_3)_2$:EDTA] and 2 mM of EDTA alone was amended to the culture flask in the laminar chamber aseptically and inoculated with aforementioned concentration of ECOBIO_2 cells. Culture flasks were observed for precipitation.

Figure 5A:
FIGS. 5A through 5C show bioavailability of chelated lead acetate (FIG. 5A), chelated lead nitrate (FIG. 5C), and non-chelated lead nitrate and lead acetate (FIG. 5B), to *B. licheniformis* strain ECOBIO_2 under in vitro conditions.
Figure 5E:
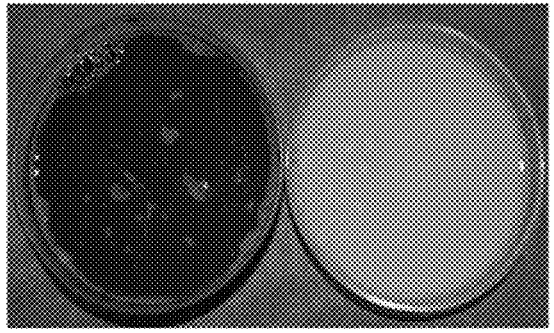
FIG. 5E shows lead precipitate effected by *B. licheniformis* strain ECOBIO_2 in a petri plate (left) and a control culture suspension without lead amendment (right).
Figure 5B:
Figure 5F:
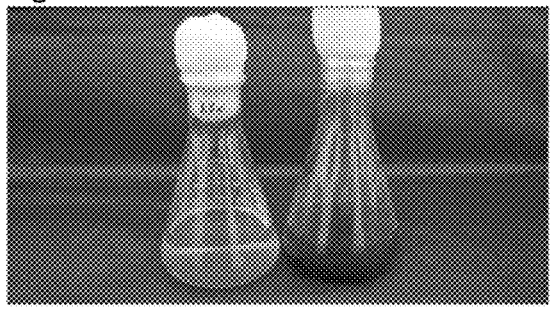
FIG. 5F shows flasks containing media comprising lead inoculated with heat killed cells (left) and viable cells (right).
Figure 5C:
Figure 5D:
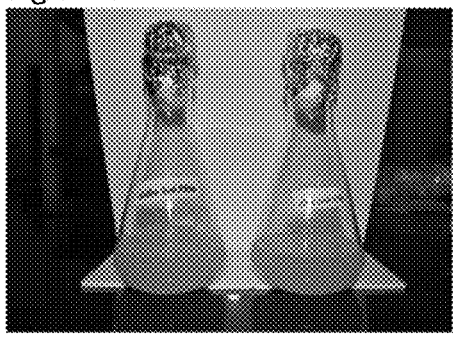
FIG. 5D shows *B. licheniformis* strain ECOBIO_2 cells growing in the presence of EDTA alone.

To ensure the solubility of metal in the LBP culture medium (table 1), the lead acceptability of B. licheniformis strain ECOBIO_2 was tested. Sodium EDTA was used to chelate the two lead salts like lead acetate and lead nitrate individually. Results are shown in FIGS. 5A through 5E. FIGS. 5A and 5C show the effect of chelated lead salts on bioavailability to B. licheniformis strain ECOBIO_2 under in vitro conditions. FIG. 5B shows the effect of non-chelated lead salts (lead nitrate and lead acetate) on bioavailability to B. licheniformis strain ECOBIO_2 under in vitro conditions. FIG. 5D shows cells growing in the presence of EDTA. FIG. 5E shows Petri plates with precipitate and control culture agar plates. FIG. 5F shows flasks inoculated with heat killed cells (left) and viable cells (right). Marked precipitation was observed only in the flasks with lead nitrate and lead acetate (FIG. 5B), and chelated lead acetate—EDTA (FIG. 5A), but not the lead nitrate complexed with EDTA (FIG. 5C). This shows the involvement of metal speciation in bioavailability of chelated metals.

Example 6

This Example illustrates the involvement of alkalinity of culture medium in mediating Pb' precipitation.

Figure 6:
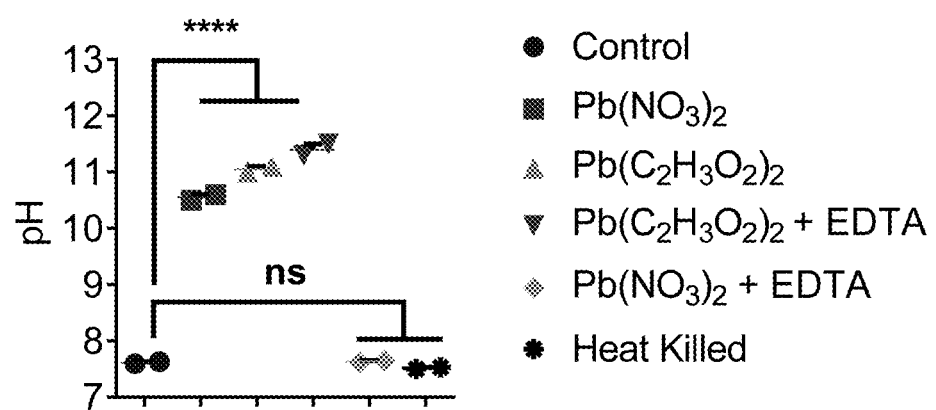
FIG. 6 shows the pH of culture broth after the recovery of bioprecipitated $Pb^{2+}$ by *B. licheniformis* strain ECOBIO_2.

The pH of culture broth after the recovery of bioprecipitated Pb' by B. licheniformis strain ECOBIO_2 was found to be 12. However, the pH of the control broth remained at 7. With this background, experiments were conducted to assess the involvement of alkalinity of the culture medium in mediating lead precipitation. Both the chelated and non-chelated forms of $Pb(C_2H_3O_2)_2$ and $Pb(NO_3)_2$ were added in culture broth and the initial pH was recorded as 7.4. Further, after the three days of incubation, individual flasks were tested for change in the pH. Results are shown in FIG. 6. To rule out the involvement of pH alone in precipitation, ammonium chloride was added to the broth amended with $Pb(NO_3)_2$+EDTA till the pH of the medium reached 12 and the broth was observed for signs of precipitation. No precipitation was observed even after increasing the pH of medium to 12 and 14. Thus the investigation confirmed that pH alone without the bacteria cannot bring forth the precipitation of lead, and that the lead precipitation is due to the bacteria and not due to the pH change.

Example 7

This Example illustrates the recovery of lead precipitated out of the medium by B. licheniformis.

Figure 7A:
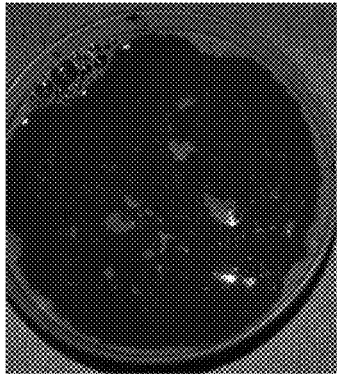
FIG. 7A shows petri plates displaying lead precipitate recovered from LBP broth due to bioremediation.
Figure 7B:
FIG. 7B shows precipitate of lead salts obtained after drying.

Culture flask with one liter of LBP broth-amended with 2 mM lead acetate was inoculated with 2.5 ml of 48 hours pre-acclimatized culture broth of B. licheniformis strain ECOBIO_2. The culture flask was incubated at room temperature without shaking for 48 hours. After 48 hours of incubation, dark black crystal formation was seen to be settled at the bottom of the culture flask. Cells were harvested by consecutive centrifugation (Eppendorf, USA) using Falcon 50 ml conical centrifuge tubes (Fisher Scientific, USA), after which pellets were frozen for overnight at −80° C. and then lysed at room temperature using Labiase 10 mg/ml bacterial lytic enzyme (Sigma-Aldrich, USA). Further, the bio-precipitates were recovered by following procedure described by Mire et al. (2004). The results are shown in FIG. 7. Petri plates displaying (A) recovered precipitant from LBP broth and (B) bio-precipitate of lead salts obtained after drying.

Lead analysis was done using inductively coupled plasma-optical emission spectrometer (ICP-OES Perkin Elmer, USA). Both the control culture broth and precipitate were evaluated to estimate the presence of lead. Ash converted samples were further dissolved in 10% nitric acid, and the filtrate was made up to 100 ml and injected to ICP-OES. The instrument was calibrated using multi-standard elements (Perkin Elmer Life and Analytical Sciences, US) with 10% nitric acid as sample blank. ICP-OES confirmed the presence of lead (760.5 mg/l). In addition, the presence of lead in the recovered precipitate was confirmed by X-ray diffraction studies.

Example 8

This example illustrates the application of B. licheniformis for bio-recovery of lead from dyeing industry effluent.

Economic feasibility and sustainability are often key concerns for in situ bioremediation. Despite huge number of metal-tolerant microbes cataloged by several groups around the world, very few efforts have been made towards assessing the potentials benefits of microbes under ex situ set-up. The present Example demonstrates ex situ bio-precipitation of $Pb^{2+}$.

A glass aquarium bowl (having a depth of 6 inches, a circumference of 18.2 inches, and a volume of 2.5 L) and a 500 mL conical flask were used to simulate performance under uncontrolled (unsterilized) and controlled (sterilized) conditions, respectively. The composition and conditions of the uncontrolled and controlled experiments are given in Table 5.

TABLE 5

Conditions of controlled and uncontrolled ex situ setup

| Constituents | Controlled | Uncontrolled |
| --- | --- | --- |
| Effluent | 100 mL | 650 mL |
| $Pb(C_2H_3O_2)_2$ | 2 mM | 2 mM |
| Water used in preparation of LBP | Sterile distilled | Tap |
| NaCl | 0.6 grams | 4.25 grams |
| Yeast extract | 0.8 grams | 8 grams |
| Casamino acids | 0.5 grams | 5 grams |
| Peptone | 1.0 grams | 6.5 grams |
| $MgSO_4$ | 0.3 grams | 3 grams |
| 48 hours pre-acclimatized inoculum | 10 mL | 30 mL |
| Incubation temperature | 37° C. at orbital shaker incubator | Room temp. (no shaking) |

Primarily, effluent stored at 4° C. was filtered to remove the suspended solids and subjected to ICP-OES analysis to determine the concentration of $Pb^{2+}$. Both the batch systems were kept for incubation and observed for the formation of fine black precipitate. Further, the precipitate was subjected to Energy-Dispersive X-Ray Spectroscopy (EDS) for the confirmation of lead in the precipitate.

Figure 8A:
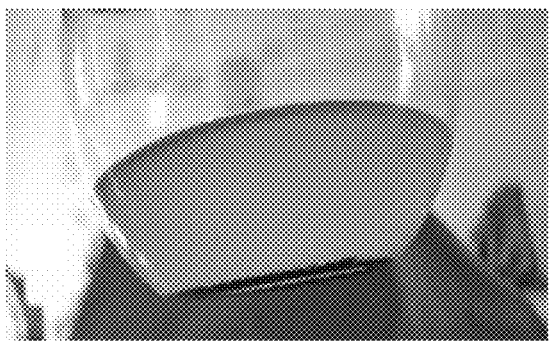
FIG. 8A shows lead precipitation observed from dyeing industrial effluent upon treatment with *B. licheniformis* strain ECOBIO_2.
Figure 8B:
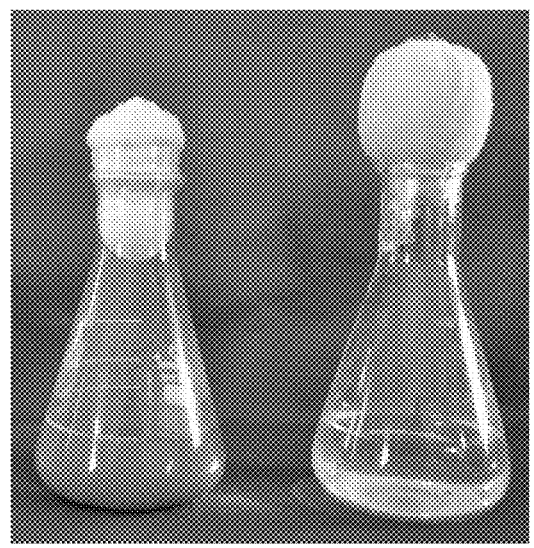
FIG. 8B shows lead bio-precipitation from industrial effluents.
Figure 9:
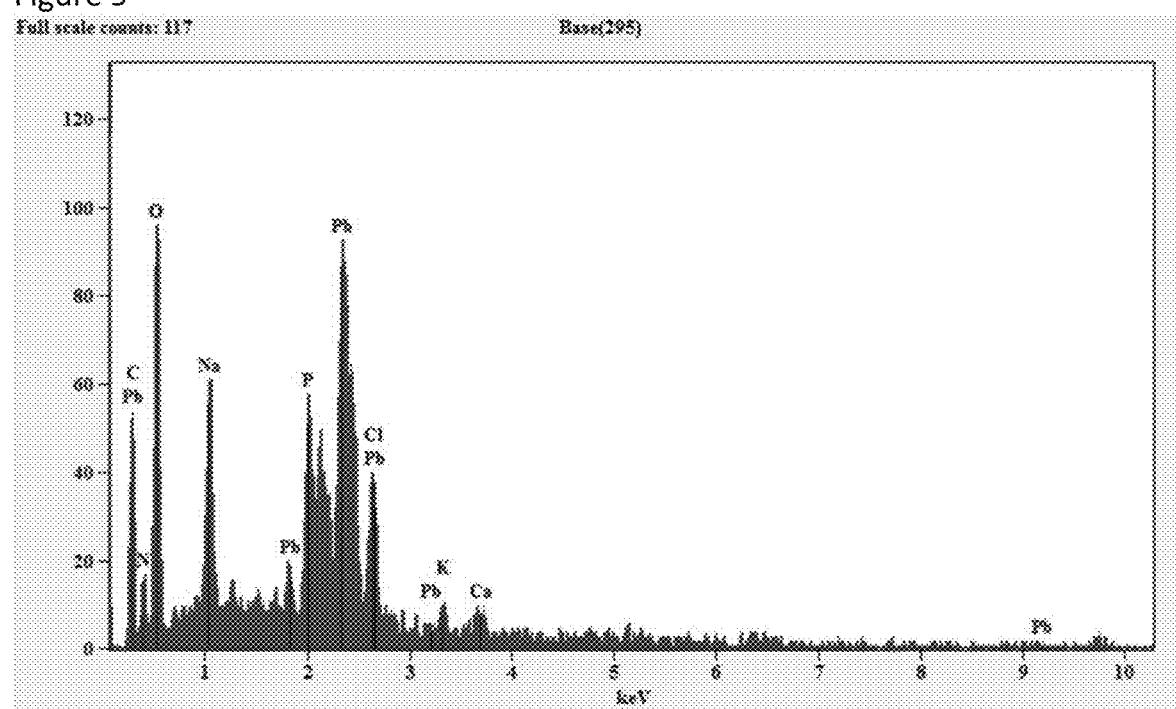
FIG. 9 shows the EDS spectra of bio-precipitate recovered from *B. licheniformis* showing the expected peak position of $K_2PbO_3$ (potassium plumbate).

The results are shown in FIGS. 8A, 8B, and 9. FIG. 8A shows lead precipitation observed from dyeing industrial effluent upon treatment with *B. licheniformis* strain ECOBIO_2. FIG. 8B shows lead bio-precipitation from industrial effluents with components mentioned in Table 4, with the conical flask (right) containing a control consisting of effluent+lead (Pb). FIG. 9 shows the EDS spectra of bio-precipitate recovered from *B. licheniformis*.

The results of these studies indicate the Pb' bio-precipitation efficiency of *B. licheniformis* strain ECOBIO_2 from the industrial effluent. The bio-precipitation in the open culture system indicates the competence of *B. licheniformis* with native microbes and its potentiality in executing the lead immobilization. This was achieved in the presence of very minimal nutrition supplement which significantly proves the ex situ efficiency of the isolate.

While various embodiments of the system have been described in detail, it is apparent that modifications and alterations of those embodiments will occur to those skilled in the art. It is to be expressly understood that such modifications and alterations are within the scope and spirit of the present disclosure. The examples are provided for the purpose of illustration and are not intended to limit the scope of the present invention. Each publication, sequence or other reference disclosed below and elsewhere herein is incorporated herein by reference in its entirety, to the extent that there is no inconsistency with the present disclosure.

The invention claimed is:

1. A method for bioremediation of a contaminated or waste material comprising lead, comprising the steps of:
   (a) inoculating *Bacillus licheniformis* bacteria having a 16S rRNA gene comprising SEQ ID NO:1 in an aqueous culture medium comprising casamino acids and lead;
   (b) growing the *Bacillus licheniformis* bacteria in the aqueous culture medium for a period of time;
   (c) contacting at least a portion of the aqueous culture medium with the contaminated or waste material; and
   (d) precipitating at least some of the lead present in the contaminated or waste material.

2. The method of claim 1, wherein the aqueous culture medium in step (c) comprises live *Bacillus licheniformis* bacteria.

3. The method of claim 1, comprising, prior to step (c), centrifuging the aqueous culture medium to obtain a supernatant fraction and a fraction enriched in the *Bacillus licheniformis* bacteria, and wherein, in step (c), the at least a portion of the aqueous culture medium comprises at least one of the supernatant fraction and the fraction enriched in the *Bacillus licheniformis* bacteria.

4. The method of claim 1, wherein, in step (c), the aqueous culture medium is provided in at least one of (i) the form of a patty and (ii) a permeable container.

5. The method of claim 1, wherein the aqueous culture medium further comprises at least one metal salt, yeast extract, and peptone.

6. The method of claim 1, wherein
   (i) the concentration of lead in the aqueous culture medium is between about 0.1 mM and about 4 mM, and/or (ii) the concentration of lead in the waste material is between about 0.1 mM and about 6 mM.

7. The method of claim 1, wherein step (b) comprises growing the bacteria for a period of at least 48 hours.

8. The method of claim 1, comprising incubating the bacteria at a temperature of about 25° C. to about 40° C.

9. The method of claim 1, wherein the pH of the aqueous culture medium is between about 5 and about 9.

10. The method of claim 1, further comprising recovering at least a portion of at least one of (i) the *Bacillus licheniformis* bacteria and (ii) the precipitated lead.

* * * * *

SEQUENCE LISTING

<160> NUMBER OF SEQ ID NOS: 1

<210> SEQ ID NO 1
<211> LENGTH: 781
<212> TYPE: DNA
<213> ORGANISM: Bacillus licheniformis

<400> SEQUENCE: 1

```
agatgggagc ttgctccctg tatgttagcg gcggacgggt gagtaacacg tgggtaacct      60
gcctgtaaga ctgggataac tccgggaaac cggggctaat accggatgct tgattgaacc     120
gcatggttca attataaaag gtggcttttta gctaccactt acagatggac ccgcggcgca     180
ttagctagtt ggtgaggtaa cggctcacca aggcaacgat gcgtagccga cctgagaggg     240
tgatcggcca cactgggact gagacacggc ccagactcct acgggaggca gcagtaggga     300
atcttccgca atggacgaaa gtctgacgga gcaacgccgc gtgagtgatg aaggtttcg      360 gatcgtaaaa ctctgttgtt agggaagaac aagtaccgtt cgaatagggc ggtaccttga     420
cggtacctaa ccagaaagcc acggctaact acgtgccagc agccgcggta atacgtaggt     480
ggcaagcgtt gtccggaatt attgggcgta aagcgcgcgc aggcggtttc ttaagtctga     540
tgtgaaagcc cccggctcaa ccggggaggg tcattggaaa ctggggaact tgagtgcaga     600
agaggagagt ggaattccac gtgtagcggt gaaatgcgta gagatgtgga ggaacaccag     660
tggcgaaggc gactctctgg tctgtaactg acgctgaggc gcgaaagcgt ggggagcgaa     720
caggattaga taccctgcta gtccacgccc gtaaacgatg agtgctaagg tgttagaggg     780
t                                                                     781
```